(12) United States Patent
Lin

(10) Patent No.: US 10,095,014 B2
(45) Date of Patent: Oct. 9, 2018

(54) OPTICAL APPARATUSES TO COLLECT THREE-DIMENSIONAL INFORMATION OF AN OBJECT

(71) Applicant: SONY CORPORATION, Tokyo (JP)

(72) Inventor: Tzunghan Lin, Taipei (TW)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/426,587

(22) Filed: Feb. 7, 2017

(65) Prior Publication Data

US 2018/0224643 A1    Aug. 9, 2018

(51) Int. Cl.

| | | |
|---|---|---|
| *G02B 17/06* | (2006.01) |
| *G02B 13/06* | (2006.01) |
| *H04N 13/00* | (2018.01) |
| *H04N 13/02* | (2006.01) |
| *H04N 13/218* | (2018.01) |
| *H04N 13/236* | (2018.01) |
| *H04N 13/254* | (2018.01) |

(52) U.S. Cl.
CPC ............. *G02B 17/06* (2013.01); *G02B 13/06* (2013.01); *H04N 13/0217* (2013.01); *H04N 13/0235* (2013.01); *H04N 13/0253* (2013.01); *H04N 13/218* (2018.05); *H04N 13/236* (2018.05); *H04N 13/254* (2018.05)

(58) Field of Classification Search
CPC .... G02B 17/06; G02B 17/0605; G02B 13/06; G02B 27/022; H04N 13/0217; H04N 13/0235; H04N 13/0253
USPC ................................ 359/850, 864; 250/215
See application file for complete search history.

(56) References Cited

U.S. PATENT DOCUMENTS 8,451,318 B2    5/2013  Trubko et al.

*Primary Examiner* — Frank Font
(74) *Attorney, Agent, or Firm* — Chip Law Group

(57) ABSTRACT

The present disclosure relates to an optical apparatus of collecting three-dimensional information of an object, which includes an optical apparatus of collecting three-dimensional information of an object, which includes an optical detector, a first omnidirectional mirror and a second omnidirectional mirror. The second omnidirectional mirror is disposed between the optical detector and the first omnidirectional mirror.

22 Claims, 4 Drawing Sheets

OPTICAL APPARATUSES TO COLLECT THREE-DIMENSIONAL INFORMATION OF AN OBJECT

BACKGROUND

Three-dimensional (3D) data collection of an object may rely on speed, accuracy, and portability for purposes such as reproduction. 3D data collection technique may be applied in fields of digital imaging, computer animation, topography, reconstructive and plastic surgery, dentistry, internal medicine, rapid prototyping, etc.

Optical apparatuses are developed to collect the shape, contour, position or other information of the object in digitized form. For example, an optical apparatus using triangulation may include two image sensors to receive light reflected from an object and then determines three-dimensional spatial locations for points where the light reflects from the object. Another type of optical apparatus, which includes merely one single image sensor, may also be provided to collect 3D information. Such optical apparatus is relatively compact as compared to the apparatus having two image sensors.

An example of a three-mirror panoramic camera is disclosed in U.S. Pat. No. 8,451,318 B2, which requires a sophisticated optical system (including three-mirror subsystem) to collect enough image data. Such three-mirror subsystem requires a relatively greater space to have a relatively greater depth of focus and may adversely affect miniaturization.

The IEEE paper (http://eia.udg.es/~qsalvi/papers/2005-ICRA.pdf) entitled "Omnidirectional Depth Computation from a Single Image" may disclose another example of a three-mirror panoramic camera, which requires highly precise alignment (calibration) of laser, a parabolic mirror, a conical mirror and a camera. Moreover, the collected image data are computed by a laser triangulation technique to determine an omnidirectional depth.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
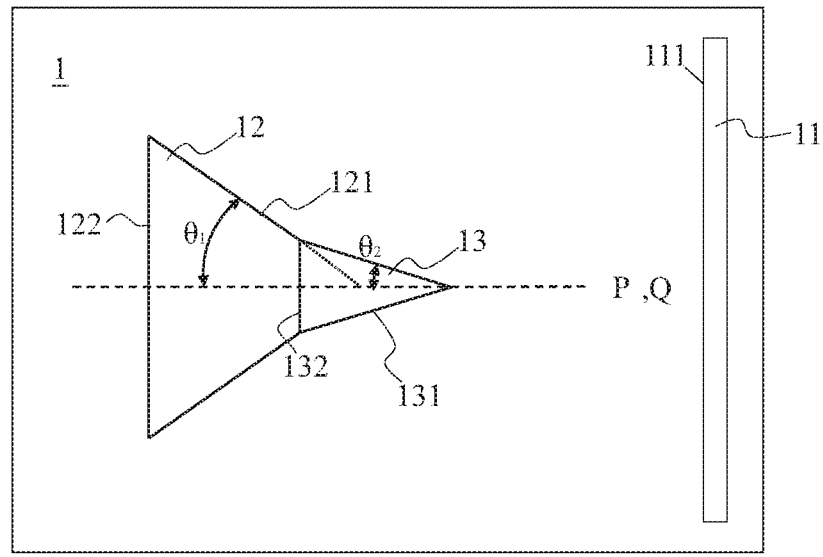
FIG. 1 illustrates an optical apparatus of collecting three-dimensional information of an object in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Referring to the figures, wherein like numerals indicate like parts throughout the several views. FIG. 1 illustrates an optical apparatus of collecting three-dimensional information of an object in accordance with some embodiments of the present disclosure.

FIG. 1 illustrates an optical apparatus of collecting three-dimensional information of an object in accordance with some embodiments of the present disclosure.

Referring to FIG. 1, an optical apparatus 1 includes an optical detector 11 and omnidirectional mirrors 12 and 13.

The optical detector 11 may be, for example but is not limited to, an image sensor, a camera, a charge coupled device (CCD) sensor, a complementary metal-oxide-semiconductor (CMOS) sensor or the like. The optical detector 11 has an image plane 111.

Each of the omnidirectional mirror 12 and 13 reflects light for any angle of incidence. The omnidirectional mirror 13 is disposed between the optical detector 11 and the omnidirectional mirror 12. The omnidirectional mirror 12 is disposed adjacent to the omnidirectional mirror 13. The omnidirectional mirror 12 is an individual piece. The omnidirectional mirror 13 is an individual piece. The omnidirectional mirror 12 is connected to the omnidirectional mirror 13.

The omnidirectional mirror 12 has an axis P (illustrated by dotted line) of symmetry. The omnidirectional mirror 12 has an optical axis P. The omnidirectional mirror 13 has an axis Q (illustrated by dotted line) of symmetry. The omnidirectional mirror 13 has an optical axis Q. The axis P overlaps the axis Q. In accordance with some embodiments of the present disclosure, the axis P does not overlap the axis Q. The omnidirectional mirror 12 is coaxial with the omnidirectional mirror 13. In accordance with some embodiments of the present disclosure, the omnidirectional mirror 12 is not coaxial with the omnidirectional mirror 13. The omnidirectional mirror 12 and the omnidirectional mirror 13 have a common axis P/Q. The optical detector 11 and omnidirectional mirrors 12 and 13 are arranged such that light reflected from the omnidirectional mirrors 12 and 13 may be received by the optical detector 11.

The omnidirectional mirror 12 has a reflection surface 121. The reflection surface 121 of the omnidirectional mirror 12 inclines at an angle $\theta_1$ to the axis P. The omnidirectional mirror 13 has a reflection surface 131. The reflection surface 131 of the omnidirectional mirror 13 inclines at an angle $\theta_2$ to the axis Q. The angle $\theta_1$ is different from the angle $\theta_2$. The angle $\theta_1$ is greater than the angle $\theta_2$. The reflection surface 121 is a planar surface. The reflection surface 131 is a planar surface.

The omnidirectional mirror 12 and the omnidirectional mirror 13 are made from one piece to form an omnidirectional reflector (not denoted in FIG. 1) which has a reflection surface 121 and a reflection surface 131. The reflection surface 121 is not co-planar with the reflection surface 131. The reflection surface 121 is adjacent to the reflection surface 131. The reflection surface 131 is formed between the reflection surface 121 and the optical detector 11. The reflection surface 121 is steeper than the reflection surface 131 with reference to a base 122 of the omnidirectional reflector.

Although it is not illustrated in FIG. 1, it is contemplated that the reflection surface 121 is a convex surface. Although it is not illustrated in FIG. 1, it is contemplated that the reflection surface 131 is a convex surface.

The omnidirectional mirror 12 has a base or bottom 122. The omnidirectional mirror 13 has a base or bottom 132. A width of the base 122 is greater than a width of the base 132.

Figure 2:
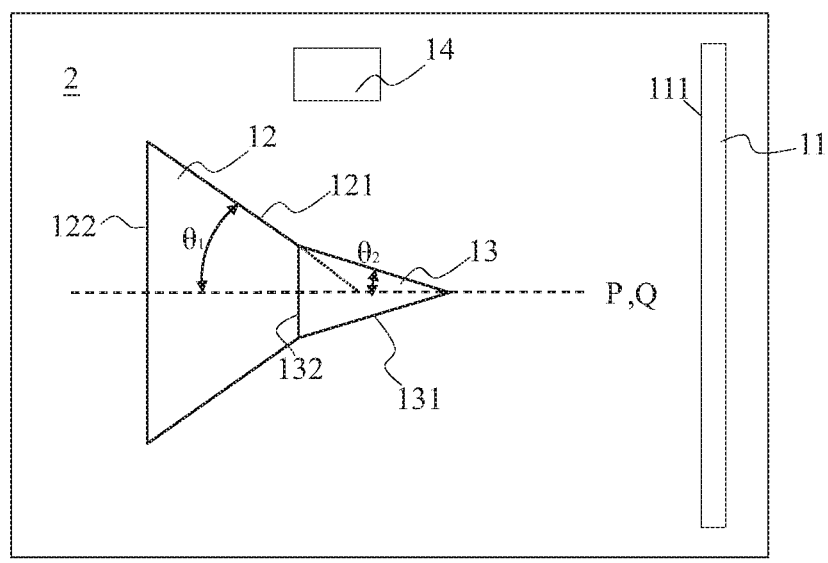
FIG. 2 illustrates another optical apparatus of collecting three-dimensional information of an object in accordance with some embodiments of the present disclosure.

FIG. 2 illustrates another optical apparatus of collecting three-dimensional information of an object in accordance with some embodiments of the present disclosure.

Referring to FIG. 2, an optical apparatus 2 is similar to the optical apparatus 1 as described and illustrated with reference to FIG. 1, except that the optical apparatus 2 further includes a light source 14. The light source 14 may include a laser. The light source 14 is disposed adjacent to the omnidirectional mirror 12 and the omnidirectional mirror 13. It is contemplated that a moving mechanism (e.g. a motor) may be added into the optical apparatus 2 to move the light source 14 though it is not illustrated in FIG. 2. It is contemplated that another moving mechanism (e.g. a motor) may be added into the optical apparatus 2 to move the optical apparatus 2 though it is not illustrated in FIG. 2.

Figure 3:
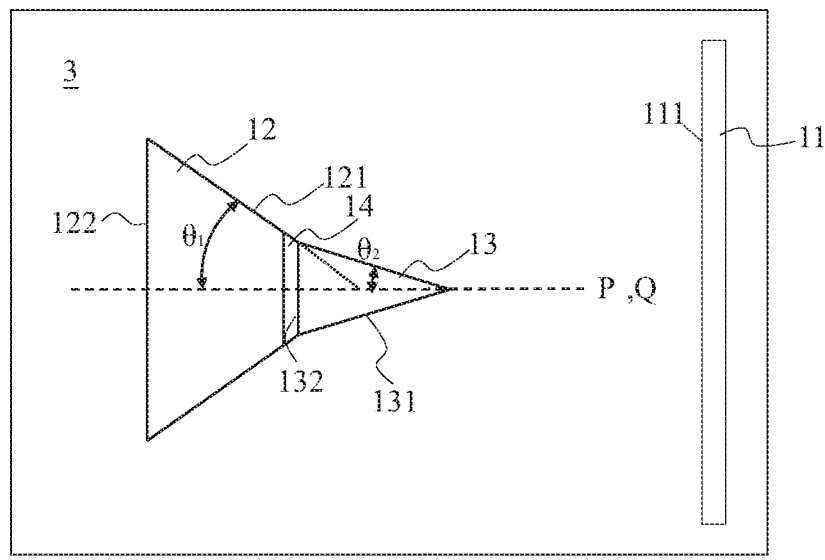
FIG. 3 illustrates another optical apparatus of collecting three-dimensional information of an object in accordance with some embodiments of the present disclosure.

FIG. 3 illustrates another optical apparatus of collecting three-dimensional information of an object in accordance with some embodiments of the present disclosure.

Referring to FIG. 3, an optical apparatus 3 is similar to the optical apparatus 2 as described and illustrated with reference to FIG. 2, except that the light source 14 is integrated with the omnidirectional mirror 12 and the omnidirectional mirror 13. The light source 14 is disposed between the omnidirectional mirror 12 and the omnidirectional mirror 13. The light source 14 has a ring shape between the omnidirectional mirror 12 and the omnidirectional mirror 13.

Figure 4:
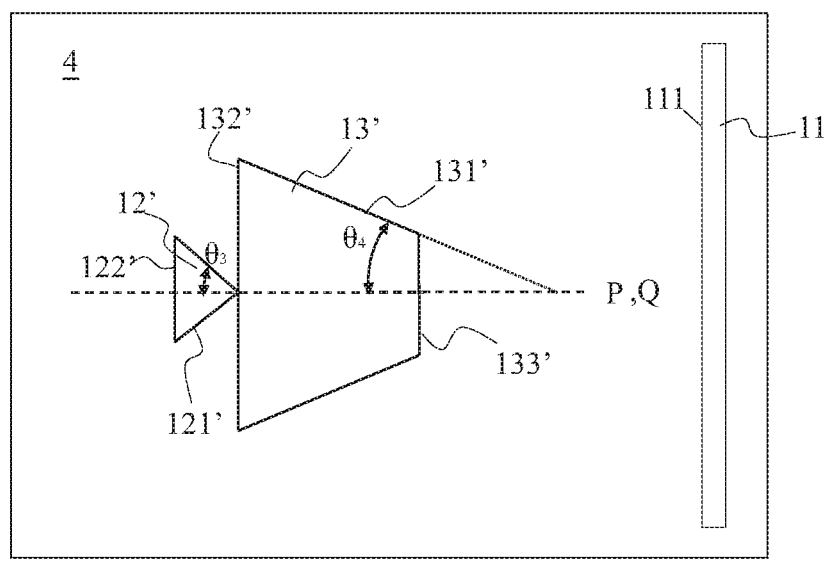
FIG. 4 illustrates another optical apparatus of collecting three-dimensional information of an object in accordance with some embodiments of the present disclosure.

FIG. 4 illustrates another optical apparatus of collecting three-dimensional information of an object in accordance with some embodiments of the present disclosure.

Referring to FIG. 4, an optical apparatus 4 includes an optical detector 11 and omnidirectional mirrors 12' and 13'.

The optical detector 11 may be, for example but is not limited to, an image sensor, a camera, a charge coupled device (CCD) sensor, a complementary metal-oxide-semiconductor (CMOS) sensor or the like. The optical detector 11 has an image plane 111.

Each of the omnidirectional mirror 12' and 13' reflects light for any angle of incidence. The omnidirectional mirror 13' is disposed between the optical detector 11 and the omnidirectional mirror 12'. The omnidirectional mirror 12' is disposed adjacent to the omnidirectional mirror 13'. The omnidirectional mirror 12' is an individual piece. The omnidirectional mirror 13' is an individual piece. The omnidirectional mirror 12' is connected to the omnidirectional mirror 13'.

The omnidirectional mirror 12' has an axis P (illustrated by dotted line) of symmetry. The omnidirectional mirror 12' has an optical axis P. The omnidirectional mirror 13' has an axis Q (illustrated by dotted line) of symmetry. The omnidirectional mirror 13' has an optical axis Q. The axis P overlaps the axis Q. In accordance with some embodiments of the present disclosure, the axis P does not overlap the axis Q. The omnidirectional mirror 12' is coaxial with the omnidirectional mirror 13'. In accordance with some embodiments of the present disclosure, the omnidirectional mirror 12' is not coaxial with the omnidirectional mirror 13'. The omnidirectional mirror 12' and the omnidirectional mirror 13' have a common axis P/Q. The optical detector 11 and omnidirectional mirrors 12' and 13' are arranged such that light reflected from the omnidirectional mirrors 12' and 13' may be received by the optical detector 11.

The omnidirectional mirror 12' has a reflection surface 121'. The reflection surface 121' of the omnidirectional mirror 12' inclines at an angle $\theta_3$ to the axis P. The omnidirectional mirror 13' has a reflection surface 131'. The reflection surface 131' of the omnidirectional mirror 13' inclines at an angle $\theta_4$ to the axis Q. The angle $\theta_3$ is different from the angle $\theta_4$. The angle $\theta_3$ is greater than the angle $\theta_4$. The reflection surface 121' is a planar surface. The reflection surface 131' is a planar surface.

The reflection surface 121' is not co-planar with the reflection surface 131'. The reflection surface 131' is formed between the reflection surface 121' and the optical detector 11. The reflection surface 121' is steeper than the reflection surface 131' with reference to a base 132' of the omnidirectional mirror 13'.

Although it is not illustrated in FIG. 4, it is contemplated that the reflection surface 121' is a convex surface or a concave surface. Although it is not illustrated in FIG. 4, it is contemplated that the reflection surface 131' is a convex surface or a concave surface.

The omnidirectional mirror 12' has a base or bottom 122'. The omnidirectional mirror 13' has a base or bottom 132'. A width of the base 122' is smaller than a width of the base 132'.

The omnidirectional mirror 13' has a top 133'. The top 133' has a width greater than that of the base 122' of the omnidirectional mirror 12'. The omnidirectional mirror 13' has a hollow structure. The top 133' and the bottom 132' of the omnidirectional mirror 13' are transparent. A glass or transparent plate (not shown in FIG. 4) is disposed at the top 133' and a pole (not shown in FIG. 4) is used to connect the omnidirectional mirror 12' to the glass or transparent plate disposed at the top 133'. Light reflected by the reflection surface 121' can pass through the omnidirectional mirror 13' and arrive at the image place 111 of the optical detector.

Although it is not illustrated in FIG. 4, it is contemplated that the omnidirectional mirror 12' may be separated from the omnidirectional mirror 13' by a distance.

Figure 5:
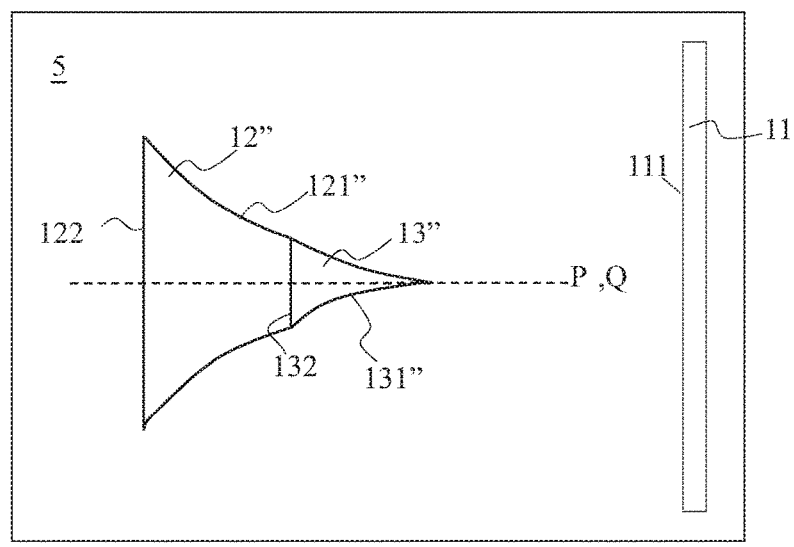
FIG. 5 illustrates another optical apparatus of collecting three-dimensional information of an object in accordance with some embodiments of the present disclosure.

FIG. 5 illustrates another optical apparatus of collecting three-dimensional information of an object in accordance with some embodiments of the present disclosure.

Referring to FIG. 5, an optical apparatus 5 is similar to the optical apparatus 1 as described and illustrated with reference to FIG. 1, except that the reflection surface 121" of the omnidirectional mirror 12" is a concave surface and the reflection surface 131" of the omnidirectional mirror 13" is a concave surface. The optical apparatus 5 provides relatively better spatial resolution due to concave reflection surfaces 121" and 131".

It is contemplated that the light source 14, which is illustrated and described with reference to FIG. 2, may be added to each of the optical apparatuses 3, 4 and 5 illustrated and described with reference to FIGS. 3, 4 and 5, respectively. It is contemplated that a moving mechanism which is similar to the moving mechanism as described with reference to FIG. 2 may be added to the optical apparatuses 3, 4 and 5 illustrated and described with reference to FIGS. 3, 4 and 5, FIG. 6 illustrates an operation of an optical apparatus in accordance with some embodiments of the present disclosure.

Figure 6:
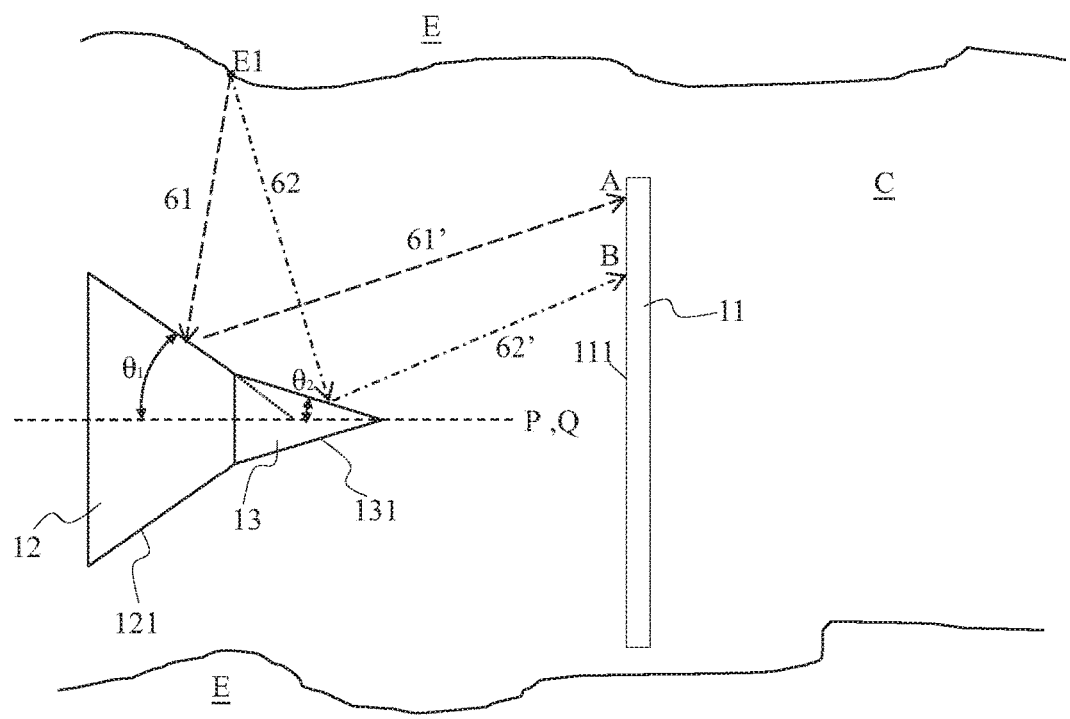
FIG. 6 illustrates an operation of an optical apparatus in accordance with some embodiments of the present disclosure.

Referring to FIG. 6, the optical apparatus 1 as shown in FIG. 1 is used to collect three-dimensional information of an object E by a single shot image. Although it is not illustrated in FIG. 6, it is contemplated that the optical apparatuses, 2, 3, 4 and 5 as described above can be used to replace the optical apparatus 1 for the collection of three-dimensional information of the object E. The object E may include an ear structure. The object E may include a rugged or irregular structure.

When the optical apparatus 1 is disposed into the ear tube or ear tunnel C, a light beam 61 from a spot E1 of the ear structure E is received by the omnidirectional mirror 12 and a light beam 62 from the same spot E1 of the ear structure E is received by the omnidirectional mirror 13. The light beam 61 coming from the spot E1 of the ear structure E incident on the reflection surface 121 of the omnidirectional mirror 12. The light beam 62 coming from the spot E1 of the ear structure E incident on the reflection surface 131 of the omnidirectional mirror 13. The reflection surface 121 of the omnidirectional mirror 12 directly reflects the light beam 61' to a position A on the image plane 111 of the optical detector 11. The reflection surface 121 of the omnidirectional mirror 12 receives the light beam 61 from the spot E1 and outs the light beam 61' to the position A on the image plane 111 of the optical detector 11. The reflection surface 131 of the omnidirectional mirror 13 directly reflects the light beam 62' to a position B on the image plane 111 of the optical detector 11. The reflection surface 131 of the omnidirectional mirror 13 receives the light beam 62 from the spot E1 and outs the light beam 62' to the position B on the image plane 111 of the optical detector 11. The position A is different from the position B on the image plane 111 of the optical detector 11. The positions A and B are geometrically different. The position A is adjacent or close to the periphery of the image plane 111. The position B is adjacent or close to the center of the image plane 111.

Although it is not illustrated in FIG. 6, however, it is contemplated that the position A may adjacent or close to the center of the image plane 111 and the position B is adjacent or close to the periphery of the image plane 111 when the optical apparatus 1 is replaced by the optical apparatus 4 as described and illustrated with reference to FIG. 4.

Figure 7A:
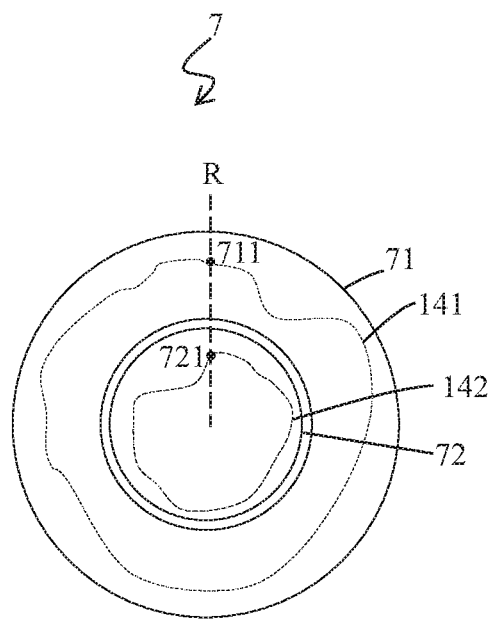
FIG. 7A illustrates an image of an optical apparatus in accordance with some embodiments of the present disclosure.

FIG. 7A illustrates an image of an optical apparatus in accordance with some embodiments of the present disclosure.

Referring to FIG. 7A, the optical apparatus, which may include an image processing software (though it is not illustrated), as described above may produce an image 7 on the image plane 111. In some embodiments, the image 7 is circular. The image 7 includes two sub-images 71 and 72. The image 7 may be decomposed into two panoramic sub-images 71 and 72 for analysis. The sub-image 71 may be formed in accordance with light beam 61'. The sub-image 72 may be formed in accordance with light beam 62'. The optical detector 11 may generate two sub-images 71 and 72. The sub-image 71 may include features 141 of light from the light source 14 and reflected by the reflection surface 121. The sub-image 72 may include features 142 of light from the light source 14 and reflected by the reflection surface 131.

Figure 7B:
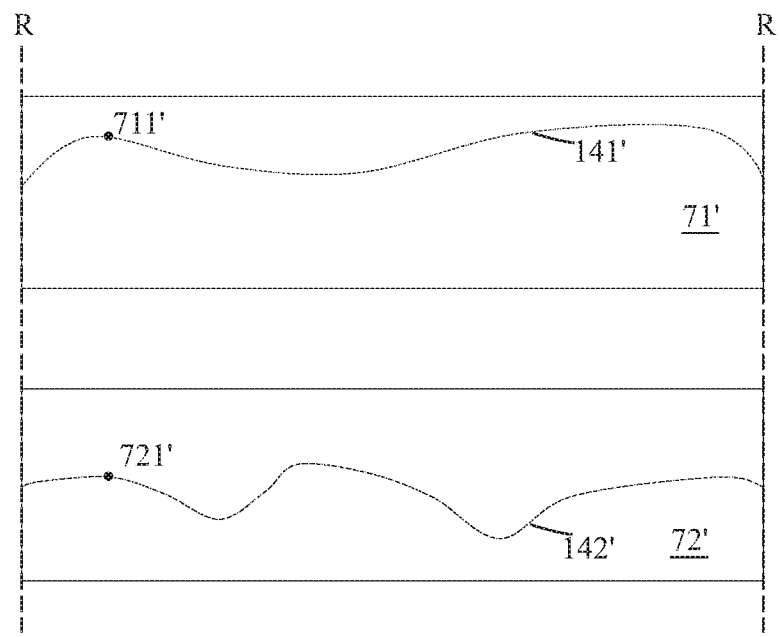
FIG. 7B illustrates an image of an optical apparatus in accordance with some embodiments of the present disclosure.

FIG. 7B illustrates an image of an optical apparatus in accordance with some embodiments of the present disclosure.

Referring to FIG. 7B, the sub-images 71 and 72 (as shown in FIG. 7A) may be unwrapped to rectangles 71' and 72' across line R (as shown in FIG. 7A). The rectangle 71' includes a number of features. The rectangle 72' includes a number of features. A pair of corresponding feature 711' and 721', which locate in rectangles 71' and 72' respectively, may include latitude information to distinguish different light beams (e.g. 61' and 62') to further determine the 3D position where the light beams come from (e.g. the spot E1 as shown in FIG. 6). Different latitudes of the feature 711' and 721' provide disparities of stereoscopy. The features 141 and 142 (as shown in FIG. 7A) may be unwrapped to features 141' and 142' across line R (as shown in FIG. 7A). The features 141' and 142' may facilitate determination of 3D position where the light beams come from (e.g. the spot E1 as shown in FIG. 6). The sub-images 71' and 72' may be processed by a triangulation method and stereoscopy technique to recover a 3D contour of the object (e.g. the object E as shown in FIG. 6).

In accordance with some embodiments of the present disclosure, an optical apparatus of collecting three-dimensional information of an object includes an optical apparatus of collecting three-dimensional information of an object, which includes an optical detector, a first omnidirectional mirror and a second omnidirectional mirror. The second omnidirectional mirror is disposed between the optical detector and the first omnidirectional mirror.

In accordance with some embodiments of the present disclosure, an optical apparatus of collecting three-dimensional information of an object, which includes an optical detector and an omnidirectional reflector. The omnidirectional reflector includes a first reflection surface and a second reflection surface. The first reflection surface is not co-planar with the second reflection surface.

In accordance with some embodiments of the present disclosure, an optical apparatus of collecting three-dimensional information of an object, which includes an optical detector, a first omnidirectional mirror and a second omnidirectional mirror. The optical detector has an image plane. The first omnidirectional mirror receives a first light beam from a spot of the object and directly reflects the first light beam to a first position on the image plane. The second omnidirectional mirror is disposed between the optical detector and the first omnidirectional mirror. The second omnidirectional mirror receives a second light beam from the same spot of the object and directly reflects the second light beam to a second position other than the first position on the image plane.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An optical apparatus to collect three-dimensional information of an object, comprising:
    an optical detector;
    a first omnidirectional mirror, wherein the first omnidirectional mirror has a reflection surface, and the reflection surface is planar; and
    a second omnidirectional mirror between the optical detector and the first omnidirectional mirror.

2. The optical apparatus of claim 1, wherein the reflection surface of the first omnidirectional mirror is inclined at a first angle to an axis of symmetry of the first omnidirectional mirror, and the second omnidirectional mirror has a reflection surface inclined at a second angle to an axis of symmetry of the second omnidirectional mirror, and wherein the first angle is different from the second angle.

3. The optical apparatus of claim 2, wherein the first angle is greater than the second angle.

4. The optical apparatus of claim 2, wherein the reflection surface of the second omnidirectional mirror is planar.

5. The optical apparatus of claim 1, further comprising a light source adjacent to the first omnidirectional mirror.

6. The optical apparatus of claim 5, wherein the light source is between the first omnidirectional mirror and the second omnidirectional mirror.

7. The optical apparatus of claim 1, wherein the second omnidirectional mirror is adjacent to the first omnidirectional mirror.

8. The optical apparatus of claim 1, wherein a base of the first omnidirectional mirror has a first width, and a base of the second omnidirectional mirror has a second width, and wherein the first width is greater than the second width.

9. The optical apparatus of claim 1, wherein a base of the first omnidirectional mirror has a first width, and a base of the second omnidirectional mirror has a second width, and wherein the first width is smaller than the second width.

10. An optical apparatus to collect three-dimensional information of an object, comprising:
    an optical detector; and
    an omnidirectional reflector that comprises:
        a first reflection surface that is planar; and
        a second reflection surface, wherein the first reflection surface is not co-planar with the second reflection surface.

11. The optical apparatus of claim 10, wherein the second reflection surface is adjacent to the first reflection surface, and wherein the second reflection surface is between the first reflection surface and the optical detector.

12. The optical apparatus of claim 10, wherein the first reflection surface is steeper than the second reflection surface with respect to a base of the omnidirectional reflector.

13. The optical apparatus of claim 10, wherein the second reflection surface is planar.

14. The optical apparatus of claim 10, further comprising a light source adjacent to the omnidirectional reflector.

15. The optical apparatus of claim 14, wherein the light source is between the first reflection surface and the second reflection surface.

16. An optical apparatus to collect three-dimensional information of an object, comprising:
    an optical detector that has an image plane;
    a first omnidirectional mirror configured to receive a first light beam from a spot of the object and reflect the first light beam directly to a first position on the image plane; and
    a second omnidirectional mirror between the optical detector and the first omnidirectional mirror, wherein the second omnidirectional mirror is configured to receive a second light beam from the same spot of the object and reflect the second light beam directly to a second position on the image plane, and wherein the second position is different from the first position on the image plane.

17. The optical apparatus of claim 16, wherein the first position is adjacent to a periphery of the image plane, and wherein the second position is adjacent to a center of the image plane.

18. The optical apparatus of claim 16, wherein the first position is adjacent to a center of the image plane, and wherein the second position is adjacent to a periphery of the image plane.

19. An optical apparatus to collect three-dimensional information of an object, comprising:
    an optical detector;
    a first omnidirectional mirror, wherein the first omnidirectional mirror has a reflection surface, and the reflection surface is concave; and
    a second omnidirectional mirror between the optical detector and the first omnidirectional mirror.

20. An optical apparatus to collect three-dimensional information of an object, comprising:
    an optical detector;
    a first omnidirectional mirror, wherein the first omnidirectional mirror has a reflection surface inclined at a first angle to an axis of symmetry of the first omnidirectional mirror; and
    a second omnidirectional mirror between the optical detector and the first omnidirectional mirror, wherein the second omnidirectional mirror has a reflection surface inclined at a second angle to an axis of symmetry of the second omnidirectional mirror, and wherein the first angle is greater than the second angle.

21. An optical apparatus to collect three-dimensional information of an object, comprising:
    an optical detector;
    a first omnidirectional mirror;
    a second omnidirectional mirror between the optical detector and the first omnidirectional mirror; and
    a light source between the first omnidirectional mirror and the second omnidirectional mirror.

22. An optical apparatus to collect three-dimensional information of an object, comprising:
    an optical detector;
    a first omnidirectional mirror; and
    a second omnidirectional mirror between the optical detector and the first omnidirectional mirror, wherein a base of the first omnidirectional mirror has a first width and a base of the second omnidirectional mirror has a second width, and wherein the first width is greater than the second width.

\* \* \* \* \*